United States Patent [19]

Hawtrey et al.

[11] 4,019,498
[45] Apr. 26, 1977

[54] DEVICE FOR CONTROL OF FEMALE URINARY INCONTINENCE

[75] Inventors: Charles E. Hawtrey; Paul Walter Vervais, both of Iowa City, Iowa

[73] Assignee: The University of Iowa Research Foundation, Iowa City, Iowa

[22] Filed: June 27, 1975

[21] Appl. No.: 590,892

[52] U.S. Cl. .......................... 128/1 R; 128/DIG. 25
[51] Int. Cl.² ......................................... A61B 19/00
[58] Field of Search ........... 128/127, DIG. 25, 341, 128/285, 270, 98, 79, 1 R; 206/438

[56] References Cited

UNITED STATES PATENTS

| 3,554,184 | 1/1971 | Habib | 128/DIG. 25 |
| 3,646,929 | 3/1972 | Bonnar | 128/DIG. 25 |
| 3,705,575 | 12/1972 | Edwards | 128/1 R |
| 3,780,730 | 12/1973 | Weisman | 128/127 |
| 3,794,029 | 2/1974 | Dulle | 128/285 |
| 3,902,493 | 9/1975 | Baier et al. | 128/270 |

Primary Examiner—Lawrence W. Trapp
Attorney, Agent, or Firm—Beveridge, DeGrandi, Kline & Lunsford

[57] ABSTRACT

An improved vaginal device for females afflicted with urinary incontinence. The device consists of a molded, resilient cellular mass of plastic or rubber-like material formed in the general shape of a mushroom and dimensioned so that when inserted into the vagina, the head of the mushroom exerts an upward thrust against the anterior wall of the vagina of sufficient magnitude to block the flow of urine through the uretha, while the stem of the mushroom is posterially positioned in the vagina resting either against the prineal body or in the posterior fornix of the vagina. For ease of insertion, the cellular mushroom-shaped body is pre-compressed and inserted in a plastic sleeve or tubing which is then sealed to maintain the device in the compressed condition until it has been inserted in proper position in the vagina. Piercing of the wall of the tubing by a needle or a scalpel will then permit the introduction of air into the sponge-like cells of the device permitting it to expand and exert the desired pressure on the uretha.

7 Claims, 6 Drawing Figures

DEVICE FOR CONTROL OF FEMALE URINARY INCONTINENCE

BACKGROUND OF THE INVENTION

A number of devices have heretofore been proposed and tried for preventing or controlling female incontinence. Typical of such devices, which have heretofore been inserted in the vagina for such purposes are those shown in U.S. Pat. Nos. 2,649,086 to Sluijter, 3,066,677 to Berry, 3,554,184 to Habbib and 3,646,929 to Bonnar. All of these prior art devices are subject to one or more recognized dis-advantages. Sluijter, for example, does not provide reliable capability of the ring-shaped device to remain in position during normal motion of the patient or convulsions of the vagina produced by coughing. The Berry device requires surgical procedures for the anchoring of a hard, inflexible device in the vagina, thereby incurring the risk of infection. The Habbib device requires a complex arrangement of belts and straps to hold the device in proper position within the vagina. Lastly, the Bonnar device employs a member supporting a flexible diaphram which is expanded by an internally positioned balloon, thus requiring an inflating tube extending out of the vagina at all times.

OBJECT OF THIS INVENTION

The object of this invention is to provide an improved female incontinence device characterized by the fact that the device may be positioned and reliably retained within the vagina without resorting to any cutting or abnormal extension of the vaginal cavity.

A particular object of this invention is to provide a female incontinence device constructed of a compressible cellular material which may be readily inserted in the vagina in a compressed condition and then released to assume a partially expanded position, wherein the device exerts the desired pressure on the uretha to control incontinence.

A particular object of the invention is to provide a female incontinence device which may be economically manufactured in commercial quantities and each device being capable of repeated use by a patient.

Other objects and advantages of this invention will become apparent to those skilled in the art from the following detailed description, taken in conjunction with the annexed sheets of drawings.

DESCRIPTION OF DRAWINGS

Referring to FIG. 1, the incontinence device embodying this invention comprises a mass of resilient cellular material having the general configuration of a mushroom. In actual practice, the device should be provided in a range of sizes from which the physician can select the appropriate size to conform to the anatomy of the particular female in whom the device is to be applied. The diameter A of the stem portion of the mushroom-shaped device can range from three-quarters of an inch to one and a quarter inches. The diameter B of the head portion of the mushroom-shaped device may range in size from one and a quarter inches to one and three-quarter inches. The height C of the stem portion of the mushroom-shaped device can vary in size from one half inch to one and three-quarters inches. Lastly, the height D of the head portion of the mushroom-shaped device can vary from one half inch to one inch in dimension. The above range of dimensions are merely typical of a variety of devices that have been tried and should not be considered as a limitation on the scope of this invention.

Referring to FIG. 2, the device 1 of FIG. 1 is shown in inserted relationship in the female vagina. In such position, the head portion 1a of the device 1 bears against the anterior wall 10a of the vagina and over-lies a substantial portion of the uretha 11 which lies immediately behind the anterior wall 10a. The stem portion 1b of the device 1 bears against the opposed wall 10b of the vagina. The height of the mushroom device is selected relative to the spacing between the posterior and anterior walls 10a and 10 b of the vagina so that the device 1, when inserted, is partially compressed and thus exerts sufficient pressure on the anterior wall 10a to close the uretha 11. When urination is desired, it may be necessary to remove the device 1 from the vagina thus permitting the uretha 11 to open and the bladder 12 to discharge. Referring to FIG. 6, there is shown an alternative positioning of the device 1 of FIG. 1 which may be preferred by some patients due to the fact that self-insertion of the device may be easier. In this position the incontinence device 1 is positioned essentially at a 90° relationship to its position in FIG. 2, with the enlarged head portion 1a of the mushroom-shaped device now compressed laterally between the anterior and posterior walls of the vagina. Again the compressive force exerted by the head portion 1a on the anterior wall 10a is sufficient to close the underlying uretha 11. The stem portion 1b then projects toward the vagina opening, facilitating handling of the device.

As previously mentioned, the incontinence device 1 is preferrably formed from a resilient cellular material such as polystyrene, polyurethane or a silicone foam. The main requirement is that the device be resiliently compressible and non-toxic to the body when inserted in the vagina. Any one of several commonly known methods of molding a cellular foam article may be utilized to form the device 1 and the method of its manufacture forms no part of this invention.

A preferred form of the invention utilizes a silicone foam formed in a two-piece plaster mold by mixing a quantity of Silastic S - 537 O R T V, a silicone foam base currently manufactured and sold by Dow Corning Corporation of Midland, MI with an appropriate amount of a catalyst supplied by the same company. The mixture is then poured into a two-piece closed plaster mold defining a mushroom-shaped cavity. The resulting mixture generates gases which expand and fill the mold with a cellular material. Preferably the resulting cells of the material are open and inter-connected. As a result, substantial compression of the finished device 1 may be produced by driving the air from the open inter-connected cells. Alternatively, if a closed cell material is employed, an axial opening 1c may be provided in the stem and head portions of device 1 to facilitate the compressibility of the device.

When employing materials such as polystyrene or polyurethane, conventional injection molding techniques may be employed with the foaming gases resulting either from a chemical additive to the resin or by direct injection of pentane or freon into the extruder. If low gas pressures are employed, then a closed cell construction will result; higher gas pressures will produce open, interconnected cells, as is well known.

In either event, the surface of the cellular device 1 is irregular, providing better frictional engagement with the rugae of the vaginal wall. More importantly, the device 1 is resiliently compressible in all directions and retains its resilience indefinitely.

Figure 1:
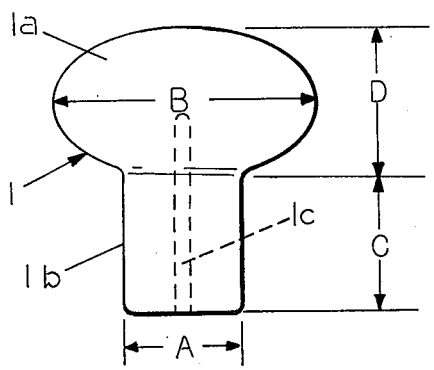
FIG. 1 is an elevational view of a typical female incontinence device enbodying this invention.
Figure 3:
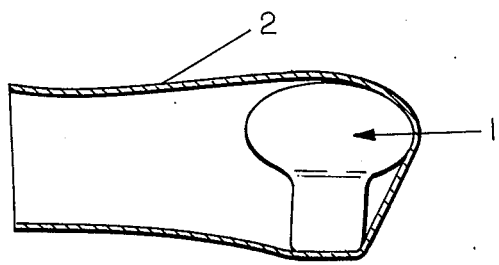
FIG. 3 is a vertical sectional of an incontinence device embodying this invention inserted in a flexible air impervious envelope for insertion purposes.
Figure 4:
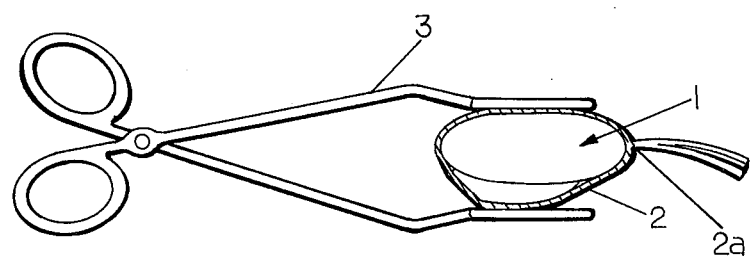
FIG. 4 illustrates the method of compressing the incontinence device to facilitate ease of insertion and the sealing of the surrounding envelope to maintain the device in compressed condition.
Figure 5:
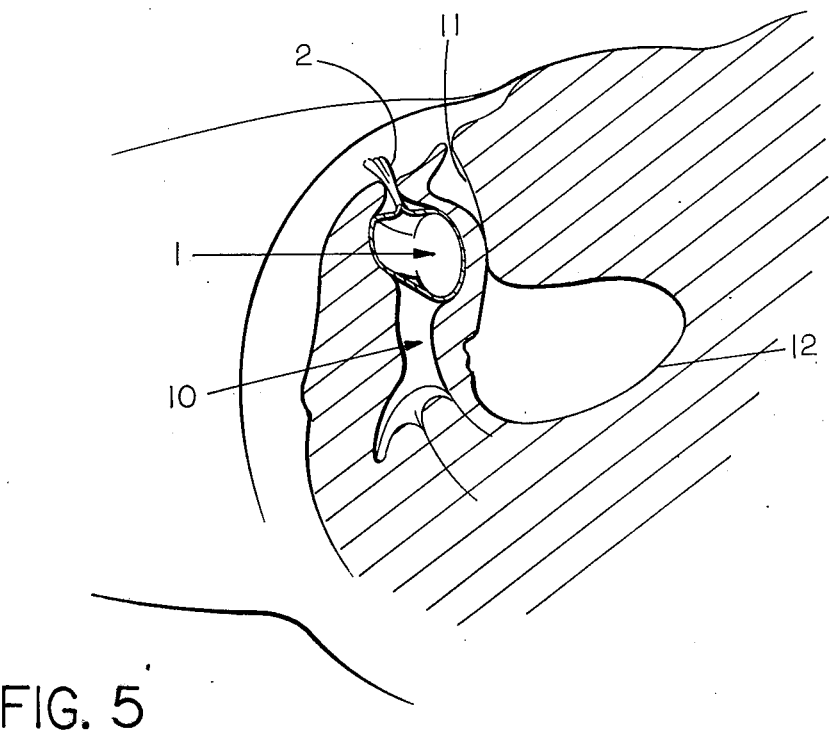
FIG. 5 is a view similar to FIG. 2 showing the envelope enclosed incontinence device inserted in the female vagina and expanded into its operative position.
Figure 2:
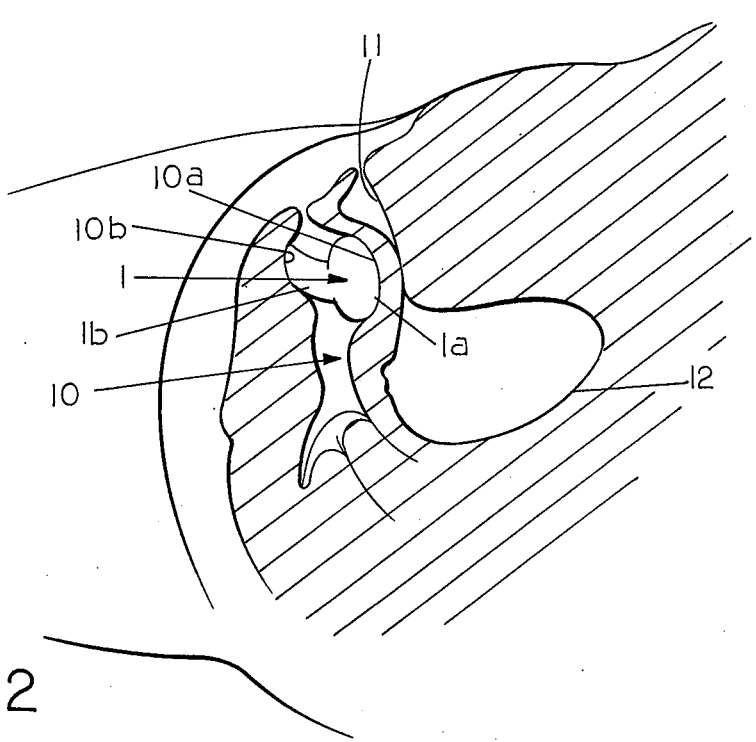
FIG. 2 is a vertical cross-sectional view of the female pelvic region showing the incontinence device embodying this invention in its inserted position.
Figure 6:
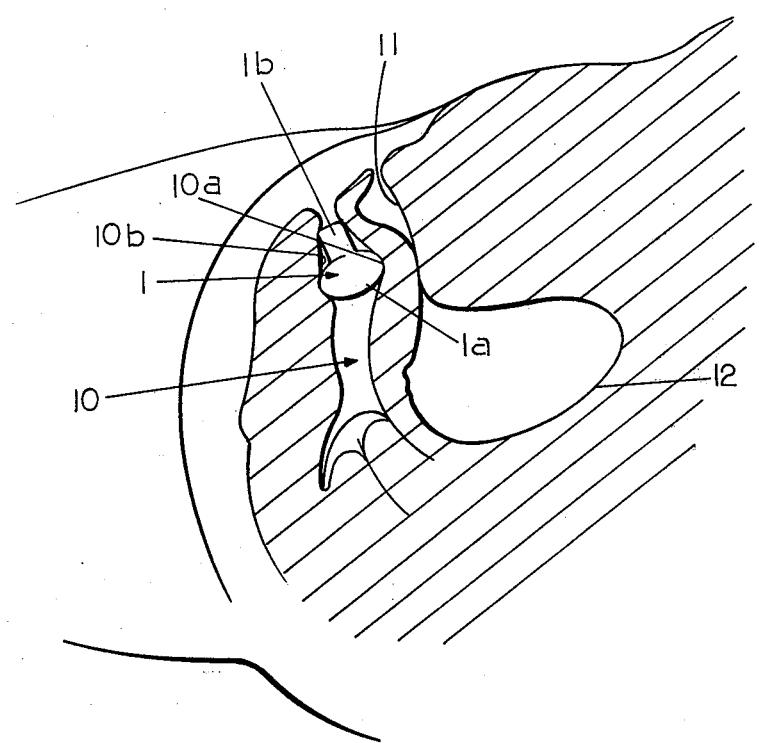
FIG. 6 is a view similar to FIG. 2 and showing an alternative position of the device of FIG. 1 in the vagina.

This compressibility feature may be conveniently utilized to effect an easier insertion of the incontinence device 1 in the vagina. Referring to FIG. 3, the device 1 is first inserted within a flexible, air-impervious envelope 2 formed from any resilient plastic or rubber-like non-toxic material such as artificial rubber, polyethylene, polypropylene or polyvinyl chloride. The device 1 is then substantially compressed by the application of the forceps 3 as illustrated in FIG. 4, thus driving the air out of the inter-connected open cells or the axial opening 1c of device 1. The envelope 2 is then sealed as indicated at 2a, either by heat sealing or by the application of a plastic tie to retain the device 1 in its compressed condition. In this condition, the device may be more easily inserted in the vagina and then the compression released on the device by piercing the envelope 2 with a needle or scalpel, thus permitting air to enter the envelope and expand the compressed device 1, as illustrated in FIG. 5.

In the initial fitting of a device 1 to a patient, the physician selects a device of the size that he estimates will be suitable for the anatomical dimensions of the particular patient. He inserts the device and the patient is asked to cough and walk about. If the device is extruded, a larger size is then selected and inserted. An acceptable device for the patient will not be extruded under the conditions of coughing, laughing and light work and, due to the resilient and spongy nature of the device 1, will be painless.

In all applications of the device to patients, all of whom were surgical failures, all thought the device embodying this invention very effective in preventing leaking of urine. The device may be repeatedly removed for cleaning and re-inserted. If the containing envelope technique is employed for insertion, then of course, the need for frequent cleaning of the device is substantially reduced.

It will be apparent to those skilled in the art that variations in configuration of the incontinence device herein disclosed may be effected without departing from the principles of the invention and the scope of this invention should be limited only in accordance with the appended claims.

We claim:

1. A device for insertion in the vagina to control incontinence comprising a solid mass of compressible cellular material having a major surface and a portion which extends to a selected distance away from said major surface, said device being of high enough compressibility and said distance being selected so that when said device is compressed and inserted in the vagina with said major surface contacting the anterior wall thereof and underlying a portion of the uretha, said portion firmly contacts the opposed wall of the vagina, and the device remains partially compressed between said anterior wall and said opposed wall with sufficient force to upwardly distend the contacted portion of the anterior vagina wall to close the uretha.

2. The device of claim 1 wherein said mass of cellular material has an enlarged head having a rounded surface and a stem portion of lesser diameter than said head, said rounded surface being said major surface and said stem portion being said portion which extends to a selected distance away from said major surface.

3. The device of claim 2 wherein said mass is formed from open-celled resilient plastic material compressible by discharge of air from said open cells.

4. The device of claim 3 plus an air impervious sealed envelope enclosing said cellular mass and holding same in said compressed condition until inserted in the vagina, whereby piercing of said envelope permits expansion of said cellular mass.

5. The device of claim 2 wherein said mass of cellular material is mushroom-shaped.

6. The device of claim 5 wherein said mushroom-shaped mass is formed from open-celled resilient plastic material compressible by discharge of air from said open cells.

7. The device of claim 6 plus an air impervious sealed envelope enclosing said cellular mass and holding same in said compressed condition until inserted in the vagina, whereby piercing of said envelope permits expansion of said cellular mass.

* * * * *